(12) United States Patent
Gleiman (10) Patent No.: US 9,084,602 B2
(45) Date of Patent: Jul. 21, 2015

(54) BUTTRESS FILM WITH HEMOSTATIC ACTION FOR SURGICAL STAPLING APPARATUS

(75) Inventor: Seth S. Gleiman, Branford, CT (US)

(73) Assignee: Covidien LP, Mansfield, MA (US)

( * ) Notice: Subject to any disclaimer, the term of this patent is extended or adjusted under 35 U.S.C. 154(b) by 123 days.

(21) Appl. No.: 13/013,977

(22) Filed: Jan. 26, 2011

(65) Prior Publication Data

US 2012/0187179 A1 Jul. 26, 2012

(51) Int. Cl.
*A61B 17/068* (2006.01)
*A61B 17/072* (2006.01)
*A61B 17/00* (2006.01)

(52) U.S. Cl.
CPC .......... *A61B 17/072* (2013.01); *A61B 17/07292* (2013.01); *A61B 17/00491* (2013.01); *A61B 2017/00889* (2013.01); *A61B 2017/00951* (2013.01); *A61B 2017/07271* (2013.01)

(58) Field of Classification Search
CPC ..... A61B 17/08; A61B 17/068; A61B 17/072
USPC ............... 227/19, 175.1, 176.1, 178.1, 180.1, 227/181.1; 606/151, 215, 219
See application file for complete search history.

(56) References Cited

U.S. PATENT DOCUMENTS

| | | |
|---|---|---|
| 3,054,406 A | 9/1962 | Usher |
| 3,124,136 A | 3/1964 | Usher |
| 3,364,200 A | 1/1968 | Ashton et al. |
| 3,666,750 A | 5/1972 | Briskin et al. |
| 3,937,223 A | 2/1976 | Roth |
| 4,347,847 A | 9/1982 | Usher |
| 4,354,628 A | 10/1982 | Green |
| 4,452,245 A | 6/1984 | Usher |
| 4,511,478 A | 4/1985 | Nowinski et al. |
| 4,605,730 A | 8/1986 | Shalaby et al. |
| 4,626,253 A | 12/1986 | Broadnax, Jr. |
| 4,655,221 A | 4/1987 | Devereux |
| 4,663,163 A | 5/1987 | Hou et al. |
| 4,826,945 A | 5/1989 | Cohn et al. |
| 4,834,090 A | 5/1989 | Moore |
| 4,838,884 A | 6/1989 | Dumican et al. |
| 4,927,640 A * | 5/1990 | Dahlinder et al. ............ 424/497 |
| 4,930,674 A | 6/1990 | Barak |

(Continued)

FOREIGN PATENT DOCUMENTS

| | | |
|---|---|---|
| CA | 2 667 434 | 5/2008 |
| DE | 1 99 24 311 A1 | 11/2000 |

(Continued)

OTHER PUBLICATIONS

International Search Report corresponding to European Application No. EP 12 15 2229.6, completed on Feb. 23, 2012 and mailed on Mar. 1, 2012; 4 pages.

(Continued)

*Primary Examiner* — Nathaniel Chukwurah (57) ABSTRACT

A surgical stapling apparatus includes a jaw assembly including a pair of jaw members and a surgical buttress positioned adjacent a tissue contacting surface of at least one of the pair of jaw members. The surgical buttress includes a hemostatic agent and is configured to release the hemostatic agent therefrom upon actuation of the surgical stapling apparatus to approximate the pair of jaw members and exert a pressure on the surgical buttress.

21 Claims, 6 Drawing Sheets

(56) References Cited

U.S. PATENT DOCUMENTS

| | | |
|---|---|---|
| 4,938,763 A | 7/1990 | Dunn et al. |
| 5,002,551 A | 3/1991 | Linsky et al. |
| 5,014,899 A | 5/1991 | Presty et al. |
| 5,040,715 A | 8/1991 | Green et al. |
| 5,065,929 A | 11/1991 | Schulze et al. |
| 5,100,992 A | 3/1992 | Cohn et al. |
| 5,160,745 A | 11/1992 | DeLuca et al. |
| 5,201,745 A | 4/1993 | Tayot et al. |
| 5,205,459 A | 4/1993 | Brinkerhoff et al. |
| 5,263,629 A | 11/1993 | Trumbull et al. |
| 5,281,197 A * | 1/1994 | Arias et al. ..................... 604/57 |
| 5,314,471 A | 5/1994 | Brauker et al. |
| RE34,742 E * | 9/1994 | Maier et al. ................. 428/36.5 |
| 5,344,454 A | 9/1994 | Clarke et al. |
| 5,392,979 A | 2/1995 | Green et al. |
| 5,397,324 A | 3/1995 | Carroll et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,505,952 A | 4/1996 | Jiang et al. |
| 5,514,379 A | 5/1996 | Weissleder et al. |
| 5,527,864 A | 6/1996 | Suggs et al. |
| 5,542,594 A | 8/1996 | McKean et al. |
| 5,549,628 A | 8/1996 | Cooper et al. |
| 5,575,803 A | 11/1996 | Cooper et al. |
| 5,580,923 A | 12/1996 | Yeung et al. |
| 5,626,863 A | 5/1997 | Hubbell et al. |
| 5,643,596 A | 7/1997 | Pruss et al. |
| 5,645,849 A | 7/1997 | Pruss et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,415 A | 4/1999 | Tucke |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,162,241 A | 12/2000 | Coury et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,358,532 B2 * | 3/2002 | Starling et al. ................. 424/489 |
| 6,376,742 B1 | 4/2002 | Zhrahala et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,592,597 B2 | 7/2003 | Grant et al. |
| 6,605,294 B2 | 8/2003 | Sawhney |
| 6,638,285 B2 | 10/2003 | Gabbay |
| 6,652,594 B2 | 11/2003 | Francis et al. |
| 6,656,193 B2 | 12/2003 | Grant |
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B2 | 8/2004 | Brauker et al. |
| 6,800,753 B2 | 10/2004 | Kumar |
| 6,818,018 B1 | 11/2004 | Sawhney |
| 6,833,408 B2 | 12/2004 | Sehl et al. |
| 6,927,315 B1 | 8/2005 | Heinecke et al. |
| 6,936,005 B2 | 8/2005 | Poff et al. |
| 6,969,400 B2 | 11/2005 | Rhee et al. |
| 7,009,034 B2 | 3/2006 | Pathak et al. |
| 7,052,713 B2 | 5/2006 | Stimmeder |
| 7,128,748 B2 | 10/2006 | Mooradian et al. |
| 7,147,138 B2 | 12/2006 | Shelton, IV |
| 7,176,256 B2 | 2/2007 | Rhee et al. |
| 7,347,850 B2 | 3/2008 | Sawhney |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,717,313 B2 | 5/2010 | Bettuchi et al. |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,909,224 B2 | 3/2011 | Prommersberger |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |

(56) References Cited

U.S. PATENT DOCUMENTS

| | | | |
|---|---|---|---|
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |
| 8,257,391 B2 | 9/2012 | Orban |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi |
| 8,308,046 B2 | 11/2012 | Prommersberger |
| 8,312,885 B2 | 11/2012 | Bettuchi |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,684,250 B2 | 4/2014 | Bettuchi |
| 8,757,466 B2 | 6/2014 | Olson |
| 8,789,737 B2 | 7/2014 | Hodgkinson |
| 8,820,606 B2 | 9/2014 | Hodgkinson |
| 2002/0016626 A1 | 2/2002 | DiMatteo et al. |
| 2002/0019187 A1 | 2/2002 | Carroll et al. |
| 2002/0028243 A1 | 3/2002 | Masters |
| 2002/0052622 A1 | 5/2002 | Rousseau |
| 2002/0091397 A1 | 7/2002 | Chen |
| 2002/0106409 A1 | 8/2002 | Sawhney et al. |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0169476 A1* | 11/2002 | Cohen .................. 606/214 |
| 2002/0177859 A1 | 11/2002 | Monassevitch et al. |
| 2003/0031697 A1 | 2/2003 | Chudzik et al. |
| 2003/0035786 A1 | 2/2003 | Hendriks et al. |
| 2003/0065345 A1 | 4/2003 | Weadock |
| 2003/0065346 A1 | 4/2003 | Evens et al. |
| 2003/0073663 A1 | 4/2003 | Wiseman et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0001879 A1 | 1/2004 | Guo et al. |
| 2004/0023842 A1 | 2/2004 | Pathak et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0101546 A1 | 5/2004 | Gorman et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0191277 A1 | 9/2004 | Sawhney et al. |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2004/0265371 A1 | 12/2004 | Looney et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0034930 A1 | 2/2006 | Khosravi et al. |
| 2006/0069337 A1* | 3/2006 | Livolsi et al. .................. 602/60 |
| 2006/0085034 A1 | 4/2006 | Bettuchi |
| 2006/0135992 A1 | 6/2006 | Bettuchi et al. |
| 2006/0159733 A1 | 7/2006 | Pendharkar et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0233869 A1 | 10/2006 | Looney et al. |
| 2006/0271104 A1 | 11/2006 | Viola et al. |
| 2007/0014862 A1 | 1/2007 | Pameijer et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123817 A1 | 5/2007 | Khosravi et al. |
| 2007/0123839 A1 | 5/2007 | Rousseau et al. |
| 2007/0179528 A1* | 8/2007 | Soltz et al. .................. 606/219 |
| 2007/0190110 A1 | 8/2007 | Pameijer et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2007/0275073 A1 | 11/2007 | Huey et al. |
| 2008/0027365 A1 | 1/2008 | Huey et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0139694 A1 | 6/2008 | Ratcliffe |
| 2008/0140115 A1 | 6/2008 | Stopek |
| 2008/0160051 A1 | 7/2008 | Sirota |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0194805 A1 | 8/2008 | Vignon et al. |
| 2008/0200949 A1 | 8/2008 | Hiles |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |

(56) References Cited

U.S. PATENT DOCUMENTS

| | | |
|---|---|---|
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0117070 A1 | 5/2009 | Daniloff et al. |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0087840 A1* | 4/2010 | Ebersole et al. ............... 606/151 |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2010/0285088 A1* | 11/2010 | Sargeant et al. ............... 424/423 |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |
| 2013/0153634 A1 | 6/2013 | Carter |
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |

FOREIGN PATENT DOCUMENTS

| | | |
|---|---|---|
| DE | 199 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 0 627 991 B1 | 10/2000 |
| EP | 1 256 318 | 11/2002 |
| EP | 1 520 525 A1 | 4/2005 |
| EP | 1702570 A1 | 9/2006 |
| EP | 1 759 640 A2 | 3/2007 |
| EP | 1 825 820 | 8/2007 |
| EP | 1815804 A2 | 8/2007 |
| EP | 1 929 958 | 6/2008 |
| EP | 2 005 895 A2 | 12/2008 |
| EP | 2008595 A2 | 12/2008 |
| EP | 2 090 231 | 8/2009 |
| EP | 2 090 244 | 8/2009 |
| EP | 2 090 252 | 8/2009 |
| EP | 2 177 239 A2 | 4/2010 |
| EP | 2 179 753 A2 | 4/2010 |
| EP | 2 198 787 A1 | 6/2010 |
| EP | 2 236 098 A2 | 10/2010 |
| EP | 2 236 099 | 10/2010 |
| EP | 2 277 458 A1 | 2/2011 |
| EP | 2 311 386 | 4/2011 |
| EP | 2 436 348 | 4/2012 |
| EP | 2 462 880 | 6/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 106 | 7/2013 |
| EP | 2 630 922 | 8/2013 |
| EP | 2 644 125 | 10/2013 |
| JP | 2000-166933 | 6/2000 |
| JP | 2002-202213 | 7/2002 |
| JP | 07-124166 | 5/2007 |
| WO | WO 90/05489 A1 | 5/1990 |
| WO | WO 94/03155 | 2/1994 |
| WO | WO 95/16221 | 6/1995 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |

(56) References Cited

FOREIGN PATENT DOCUMENTS

| WO | WO 03/088845 | 10/2003 |
|---|---|---|
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2008/057281 A2 | 5/2008 |
| WO | WO 2008/109125 A1 | 9/2008 |
| WO | WO 2010/043980 A2 | 4/2010 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

International Search Report corresponding to European Application No. EP 12 15 0511.9, completed on Apr. 16, 2012 and mailed on Apr. 24, 2012; 7 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
European Search Report corresponding to European Application No. EP 06 00 4598, completed on Jun. 22, 2006; 2 pages.
European Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2008/002981, completed on Jun. 9, 2008 and mailed on Jun. 26, 2008; 2 pages.
European Search Report corresponding to European Application No. EP 08 25 1779, completed on Jul. 14, 2008 and mailed on Jul. 23, 2008; 5 pages.
European Search Report corresponding to European Application No. EP 08 25 1989.3, completed on Mar. 11, 2010 and mailed on Mar. 24, 2010; 3 pages.
European Search Report corresponding to European Application No. EP 05 80 4382.9, completed on Oct. 5, 2010 and mailed on Oct. 12, 2010; 3 pages.
European Search Report corresponding to European Application No. EP 10 25 1437.9, completed on Nov. 22, 2010 and mailed on Dec. 16, 2010; 3 pages.
European Search Report issued in European Patent Application No. EP 09 252 417.2 mailed on Dec. 10, 2010 (3 pages).
European Search Report issued in European Patent Application No. EP 09 252 421.4 mailed on Dec. 10, 2010 (3 pages).
European Search Report corresponding to European Application No. EP 09 25 2897.5, completed on Feb. 7, 2011 and mailed on Feb. 15, 2011; 3 pages.
European Search Report for EP 12152541.4-1269 date of completion is Apr. 23, 2012 (10 pages).
Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
Extended European Search Report corresponding to EP 12 19 1035.0, completed Jan. 11, 2013 and mailed Jan. 18, 2013; 7 pages.
Extended European Search Report corresponding to EP 12 19 6904.2; completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 13 15 6297.7, completed Jun. 4, 2013 and mailed Jun. 13, 2013; 7 pages.
Extended European Search Report corresponding to EP 13 17 3985.6, completed Aug. 19, 2013 and mailed Aug. 28, 2013; 6 pages.
Extended European Search Report corresponding to EP 13 17 3986.4, completed Aug. 20, 2013 and mailed Aug. 29, 2013; 7 pages.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
Extended European Search Report corresponding to EP 08 72 6500.5, completed Feb. 20, 2014 and mailed Mar. 3, 2014; (7 pp).
Extended European Search Report corresponding to EP 13 19 5919.9, completed Feb. 10, 2014 and mailed Mar. 3, 2014; (7 pp).
Extended European Search Report corresponding to EP 13 19 2123.1, completed Jan. 30, 2014 and mailed Feb. 10, 2014; (8 pp).
Extended European Search Report corresponding to EP 13 19 6816.6, completed Mar. 28, 2014 and mailed Apr. 9, 2014; (9 pp).
Extended European Search Report corresponding to EP 13 19 4995.0, completed Jun. 5, 2014 and mailed Jun. 16, 2014; (5 pp).
Extended European Search Report corresponding to EP 13 19 5019.8, completed Mar. 14, 2014 and mailed Mar. 24, 2014; (7 pp).
Extended European Search Report corresponding to EP 13 19 2111.6, completed Feb. 13, 2014 and mailed Feb. 27, 2014; (10 pp).
Extended European Search Report corresponding to EP 13 19 7958.5, completed Apr. 4, 2014 and mailed Apr. 15, 2014; (8 pp).
Extended European Search Report corresponding to EP 14 15 6342.9, completed Jul. 22, 2014 and mailed Jul. 29, 2014; (8 pp).
Extended European Search Report corresponding to EP 14 15 7195.0, completed Jun. 5, 2014 and mailed Jun. 18, 2014; (9 pp).

* cited by examiner

BUTTRESS FILM WITH HEMOSTATIC ACTION FOR SURGICAL STAPLING APPARATUS

BACKGROUND

1. Technical Field

The present disclosure relates to surgical buttresses which can be releasably attached to a surgical stapling apparatus, and in particular, to surgical buttresses containing a hemostatic agent that is activated upon firing of the surgical stapling apparatus.

2. Background of Related Art

Surgical stapling instruments are employed by surgeons to sequentially or simultaneously apply one or more rows of fasteners, e.g., staples or two-part fasteners, to body tissue for the purpose of joining segments of body tissue together. Such devices generally include a pair of jaws or finger-like structures between which the body tissue to be joined is placed. When the stapling device is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the device to cut the tissue between the lines of staples.

When stapling certain tissue, such as lung, esophageal, intestinal, duodenal, and vascular tissues, or relatively thin or fragile tissues, it is important to effectively seal the staple line against air or fluid leakage. Preventing or reducing air or fluid leakage can significantly decrease post operative recovery time. Additionally, it is often necessary to reinforce the staple line against the tissue to prevent tears in the tissue or pulling of the staples through the tissue. One method of preventing tears or pull throughs involves the placement of a biocompatible fabric reinforcing material, or "buttress" material, between the staple and the underlying tissue.

Some buttress materials utilize hemostatic agents to reduce blood leakage. However, in some instances, it would be desirable to provide a buttress material with a protected hemostatic agent that is released upon actuation of the stapler thereby ensuring that the hemostatic agent is directed and targeted to discharge at the surgical wound site thereby enhancing sealing thereat.

SUMMARY

According to an aspect of the present disclosure, a surgical stapling apparatus includes a jaw assembly including a pair of jaw members, and a surgical buttress positioned adjacent a tissue contacting surface of at least one of the pair of jaw members. The surgical buttress includes a hemostatic agent and is configured to release the hemostatic agent therefrom upon actuation of the surgical stapling apparatus to approximate the pair of jaw members and exert a pressure on the surgical buttress.

In embodiments, the surgical buttress includes a plurality of microbeads. Each microbead has a polymeric casing defining a core containing the hemostatic agent therewithin. The polymeric casing may be fabricated from a bioabsorbable material. In embodiments, the microbeads are about 0.01 mm to about 3.0 mm in diameter. In some embodiments, the microbeads are less than about 1.0 mm in diameter. The microbeads may be configured in a variety of shapes, such as spherical, ellipsoid, elongated ellipsoid, capsule, and combinations thereof.

The hemostatic agent may be disposed within the surgical buttress in a non-solid state. In embodiments, the hemostatic agent is freely admixed with a polymer forming the surgical buttress. In some embodiments, the hemostatic agent is tethered to a polymer forming the surgical buttress. In other embodiments, the hemostatic agent is disposed within reservoirs formed within the surgical buttress.

The surgical buttress may further include a sealant and be configured to release the sealant upon actuation of the surgical stapling apparatus to approximate the pair of jaw members and exert a pressure on the surgical buttress.

The surgical buttress may further include a bioactive agent and be configured to release the bioactive agent upon actuation of the surgical stapling apparatus to approximate the pair of jaw members and exert a pressure on the surgical buttress.

The surgical buttress may be layered. In embodiments, the surgical buttress may include a first layer containing the hemostatic agent and a second layer of non-porous material positioned adjacent to the first layer. In some embodiments, the surgical buttress may also include a third layer porous or non-porous material positioned adjacent to the first layer.

According to another aspect of the present disclosure, a surgical stapling apparatus includes a jaw assembly, a trigger, and a surgical buttress. The jaw assembly includes a staple forming anvil jaw member and a staple cartridge jaw member. The trigger actuates the jaw assembly between an open position where the anvil jaw member and the staple cartridge jaw member are spaced apart from one another and a closed position where the anvil jaw member and the staple cartridge jaw member are substantially adjacent to one another, and applies at least one row of staples to tissue when the jaw assembly is in the closed position. The surgical buttress is positioned adjacent a tissue contacting surface of at least one of the anvil jaw assembly or the staple cartridge jaw assembly. The surgical buttress contains a hemostatic agent and is configured to release the hemostatic agent subsequent to actuation of the trigger and approximation of the jaw assembly to the closed position.

In embodiments, when the jaw assembly is disposed in the closed position, about 10% to about 95% of the hemostatic agent is released. In some embodiments, about 70% to about 90% of the hemostatic agent is release. The hemostatic agent may be released in response to a compressive force of the jaw assembly against tissue positioned between the anvil jaw member and the staple cartridge jaw member. The hemostatic agent may be release upon passage of a staple from a staple cartridge loaded in the staple cartridge jaw member through the surgical buttress.

According to yet another aspect of the present disclosure, a staple cartridge includes a staple cartridge containing a plurality of staples for use in a surgical stapling apparatus, and a surgical buttress disposed on a tissue contacting surface of the staple cartridge and releasably affixed to the staple cartridge. The surgical buttress includes a layer of polymeric material including a hemostatic agent and is configured to release the hemostatic agent therefrom upon application of pressure thereto.

In embodiments, the surgical buttress includes a plurality of microbeads. Each microbead has a polymeric casing defining a core containing the hemostatic agent therewithin. In embodiments, the microbeads are disposed within the layer of polymeric material. In some embodiments, the microbeads are disposed on a surface of the layer of polymeric material. The surgical buttress may include a second layer of polymeric material adjacent the layer of polymeric material including the hemostatic agent.

BRIEF DESCRIPTION OF THE DRAWINGS

Embodiments of the presently disclosed surgical stapling apparatus and surgical buttress are described herein with reference to the accompanying drawings, wherein.

DETAILED DESCRIPTION OF THE EMBODIMENTS

Various exemplary embodiments of the present disclosure are discussed herein below in terms of buttresses for use with surgical staplers. The buttresses described herein may be used in sealing a wound by approximating the edges of wound tissue between a staple cartridge and an anvil of a stapling apparatus which contains at least one buttress including a hemostatic agent protected within the buttress material. Firing of the stapling apparatus forces the legs of at least one staple to pass through the opening on the staple cartridge, the at least one buttress, tissue, and the openings on the anvil to seal the tissue. The compressive force of the anvil against the staple cartridge and/or the openings created by the passage of the staple legs through the buttress may cause the hemostatic agent to be released into the tissue advantageously reducing bleeding, assisting in sealing the wound, and allowing tissue ingrowth, if desired. Thus, the present disclosure describes surgical buttresses, and methods and mechanisms for using the same, for the targeted delivery of active or passive hemostatic agents to a specific surgical site.

While the surgical buttresses are discussed in conjunction with surgical stapling apparatus, it is envisioned that the principles of the present disclosure are equally applicable to a range of buttressing materials and film-based medical devices that are used to mechanically support tissues, reinforce tissues along staple or suture lines, and decrease the incidence of fluid leakage and bleeding of tissue.

Embodiments of the presently disclosed surgical buttress and surgical stapling apparatus will now be described in detail with reference to the drawing figures wherein like reference numerals identify similar or identical elements. In the following discussion, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is further from the clinician during proper use. As used herein, the term "patient" should be understood as referring to a human subject or other animal, and the term "clinician" should be understood as referring to a doctor, nurse or other care provider and may include support personnel.

Figure 1:
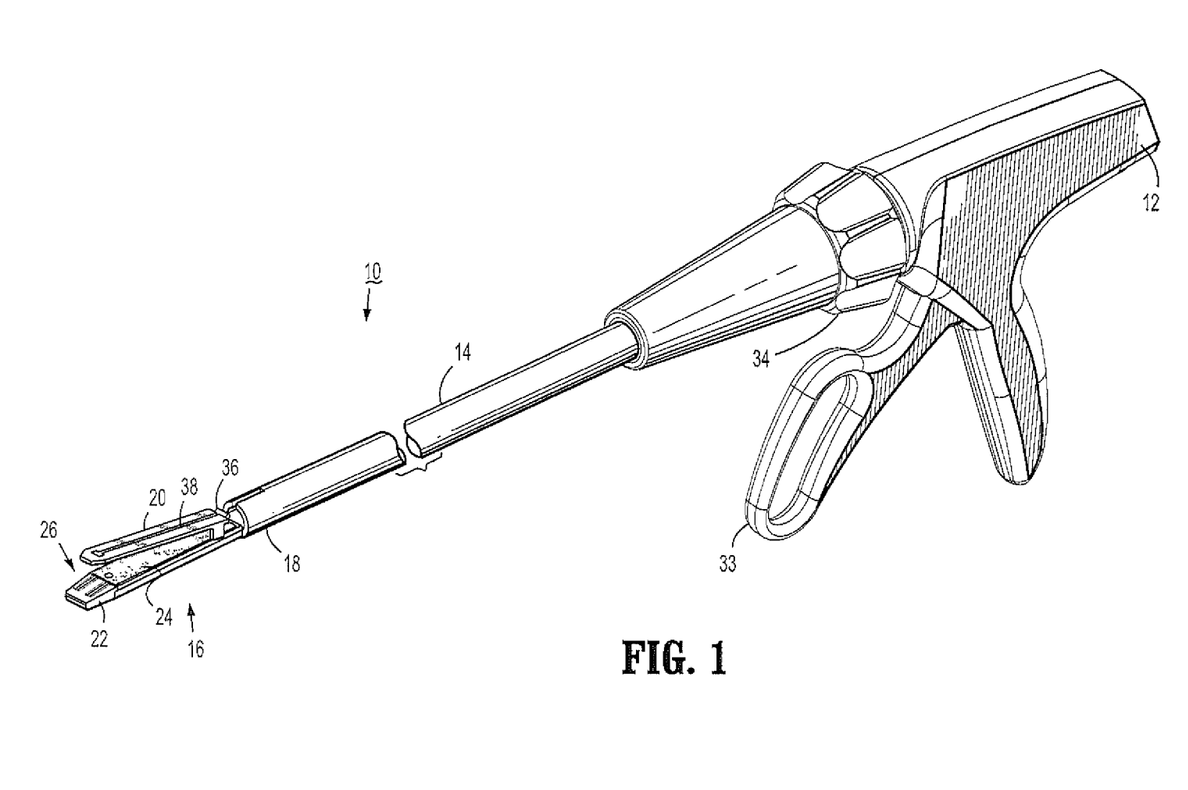
FIG. 1 is a perspective view of an illustrative embodiment of a surgical stapling apparatus including a surgical buttress in accordance with an embodiment of the present disclosure.
Figure 2:
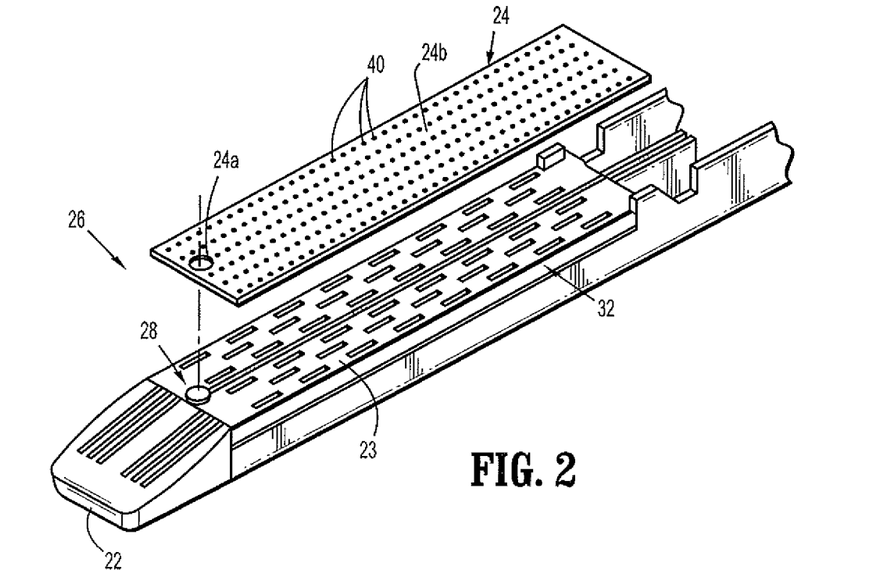
FIG. 2 is a perspective view, with parts separated, of a staple cartridge of the surgical stapling apparatus and of the surgical buttress of FIG. 1.

Referring now to FIGS. 1 and 2, there is disclosed an exemplary surgical stapling apparatus or surgical stapler 10 for use in stapling tissue and applying a buttress material or surgical buttress to the tissue. It should be understood that surgical stapling apparatus having linear stapler configurations may be utilized, such as, for example those including Duet TRS™ reloads and staplers with Tri-Staple™ technology, available through Covidien, which maintain a principal place of business at 555 Long Wharf Drive, North Haven, Conn. 06511. It should also be appreciated that the principles of the present disclosure are equally applicable to surgical staplers having alternate configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference) and laparoscopic staplers (see, e.g., commonly owned U.S. Pat. Nos. 6,330,965 and 6,241,139, each entitled "Surgical Stapling Apparatus," the entire contents of each of which being incorporated herein by this reference).

Surgical stapling apparatus 10 generally includes a handle 12 having an elongate tubular member 14 extending distally from handle 12. A jaw assembly 16 is mounted on a distal end 18 of elongate tubular member 14. Jaw assembly 16 includes a staple clinching anvil jaw member 20 and a receiving jaw member 22 configured to receive a staple cartridge 32 (see FIG. 2). Jaw assembly 16 may be permanently affixed to elongate tubular member 14 or may be detachable and thus replaceable with a new jaw assembly 16. Staple clinching anvil jaw member 20 is movably mounted on distal end 18 of jaw assembly 16 and is movable between an open position spaced apart from staple cartridge jaw member 22 to a closed position substantially adjacent staple cartridge jaw member 22.

Surgical stapling apparatus 10 further includes a trigger 33, as seen in FIG. 1, movably mounted on handle 12. Actuation of trigger 33 initially operates to move anvil jaw member 20 from the open to the closed position relative to staple cartridge jaw member 22 and subsequently actuate surgical stapling apparatus 10 to apply lines of staples to tissue. In order to properly orient jaw assembly 16 relative to the tissue to be stapled, surgical stapling apparatus 10 is additionally provided with a rotation knob 34 mounted on handle 12. Rotation of rotation knob 34 relative to handle 12 rotates elongate tubular member 14 and jaw assembly 16 relative to handle 12 so as to properly orient jaw assembly 16 relative to the tissue to be stapled.

Figure 4:
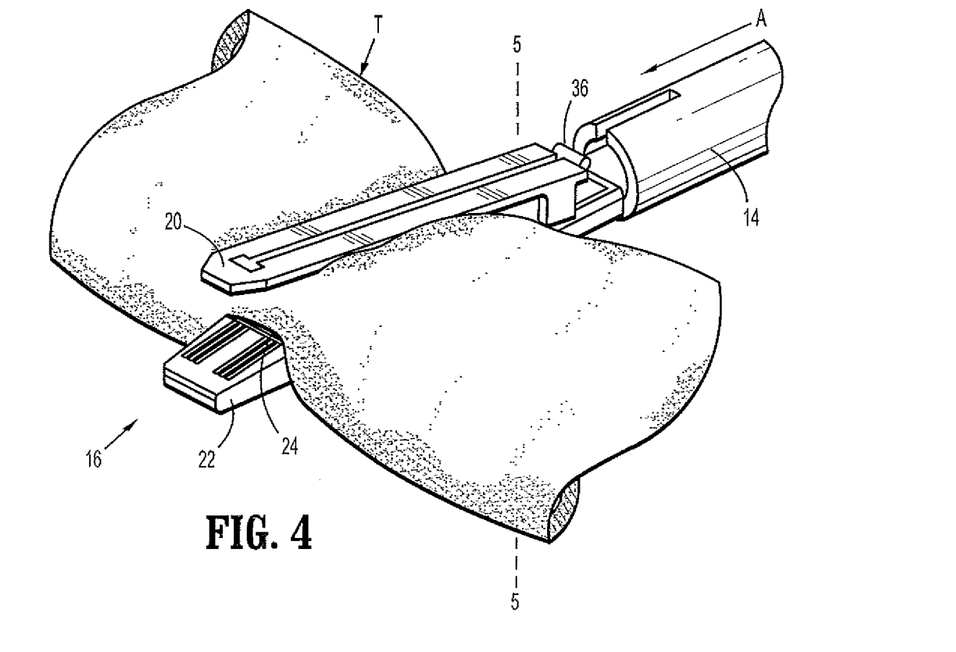
FIG. 4 is a perspective view of a distal end of the surgical stapling apparatus of FIG. 1, shown in use positioned about a tissue section.
Figure 5:
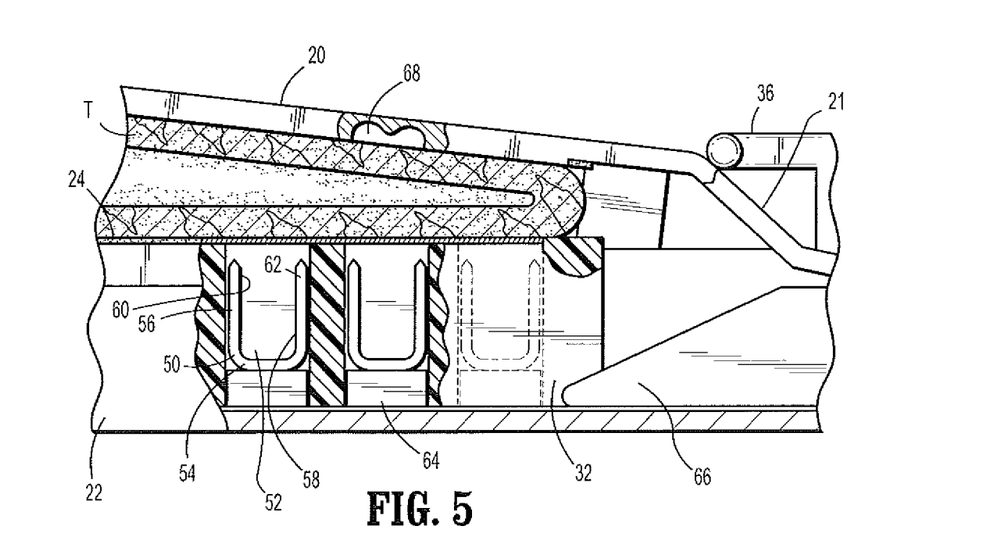
FIG. 5 is a cross-sectional view taken along line 5-5 of FIG. 4.

A driver 36, as seen in FIGS. 4 and 5, is provided to move anvil jaw member 20 between the open and closed positions relative to staple cartridge jaw member 22. Driver 36 moves between a longitudinal slot 38 (FIG. 1) formed in anvil jaw member 20. A knife blade (not shown) is associated with driver 36 to cut tissue captured between anvil jaw member 20 and staple cartridge jaw member 22 as driver 36 passes through slot 38.

Reference may be made to commonly owned U.S. Pat. No. 5,915,616, entitled "Surgical Fastener Applying Apparatus," and commonly owned U.S. Pat. Nos. 6,330,965 and 6,241,139, each entitled "Surgical Stapling Apparatus," the entire contents of each of which being incorporated herein by this reference, for a detailed discussion of the construction and operation of surgical stapling apparatus 10.

Staple clinching anvil jaw member 20 and/or staple cartridge jaw member 22 may be provided with a surgical buttress 24. It should be understood that a surgical buttress may be associated with the staple cartridge jaw member 22, the anvil jaw member 20, and/or the staple cartridge 32. Surgical buttress 24 is provided to reinforce and seal staple lines applied to tissue by surgical stapling apparatus 10. Surgical buttress 24 may be configured into any shape, size or dimension suitable to fit any surgical stapling, fastening or firing apparatus.

As illustrated in the current embodiment and shown in FIG. 2, a buttress retention system 26 is incorporated into the staple cartridge 32 to releasably secure the surgical buttress 24 to the staple cartridge 32. It is envisioned that buttress retention system 26 may additionally or alternatively be incorporated into anvil jaw member 20 such that a surgical buttress 24 may be releasably secured to anvil jaw member 20.

Buttress retention system 26 is configured to allow the surgical buttress 24 to be localized on an inwardly facing surface 23 of staple cartridge 32 in order to facilitate passage of surgical stapling apparatus 10 into the body of a patient without risk of tearing or wrinkling of the surgical buttress 24 as surgical stapling apparatus 10 is inserted into and manipulated within the body of a patient. As illustrated, buttress retention system 26 includes at least one pin 28 located on the staple cartridge 32 that is designed to releasably attach surgical buttress 24 to staple cartridge 32 via at least one hole 24a formed in the surgical buttress 24 that is shaped and designed to frictionally fit onto the pin 28. It is envisioned that the surgical buttress 24 may be releasably attached to the staple cartridge 32 and/or the anvil jaw member 20 in any manner capable of retaining the surgical buttress 24 in contact with the staple cartridge 32 and/or the anvil jaw member 20 prior to and during the stapling process, while allowing the surgical buttress 24 to be removed or released from the staple cartridge 34 and/or the anvil jaw member 20 following the penetration of the surgical buttress 24 by a surgical staple 50 (see FIG. 5) or other fastening device. For example, the surgical buttress 24 may be attached to the staple cartridge 32 and/or the anvil jaw member 20 by mechanical and/or chemical means within the purview of those skilled in the art, including, for example, adhesives, sealants, glues, pins, tacks, tabs, clamps, channels, straps, protrusions, and combinations thereof.

Surgical buttress 24 is fabricated from a layer of biocompatible material which is a bioabsorbable or non-absorbable, natural or synthetic material. It should of course be understood that any combination of natural, synthetic, bioabsorbable, and non-bioabsorbable materials may be used to form the surgical buttress.

The surgical buttress 24 may be porous, non-porous, or combinations thereof. It is also envisioned that surgical buttress 24 described herein may contain a plurality of layers in which any combination of non-porous and porous layers may be configured as discussed further below. For example, surgical buttress may be aimed to include multiple non-porous layers and porous layers that are stacked in an alternating manner. In another example, surgical buttress may be formed in a "sandwich-like" manner wherein the outer layers of the surgical buttress include porous layers and the inner layers are non-porous layers. It is further envisioned that non-porous and porous layers may be positioned in any order relative to the tissue contacting surfaces of staple cartridge jaw member and anvil jaw member. Examples of multilayered surgical buttresses are disclosed in U.S. Patent Application Publication No. 2009/0001122 filed Jun. 27, 2007, entitled "Buttress and Surgical Stapling Apparatus," the entire disclosure of which is incorporated by reference herein.

Some non-limiting examples of materials from which non-porous and/or porous layers of surgical buttress 24 may be made include but are not limited to poly(lactic acid), poly (glycolic acid), poly(hydroxybutyrate), poly(phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming a non-porous layer of the surgical buttress. Suitable natural biological polymers include, but are not limited to, collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethyl cellulose, chitan, chitosan, and combinations thereof. In addition, the natural biological polymers may be combined with any of the other polymeric materials described herein to produce a non-porous layer of the surgical buttress.

In embodiments, collagen of human and/or animal origin, e.g., type I porcine or bovine collagen, type I human collagen or type III human collagen, may be used to form a non-porous layer of the surgical buttress. In embodiments, a non-porous layer of the surgical buttress according to the present disclosure is made of collagen which is oxidized or a mixture in any proportions of non-oxidized and oxidized collagens.

The use of non-porous layer(s) in the surgical buttress may enhance the ability of the surgical buttress to resist tears and perforations during the manufacturing, shipping, handling and stapling processes. Also, the use of a non-porous layer in the surgical buttress may also retard or prevent tissue ingrowth from surrounding tissues thereby acting as an adhesion barrier and preventing the formation of unwanted scar tissue. Thus, in embodiments, the non-porous layer(s) of the surgical buttress may possess anti-adhesion properties.

A non-porous layer of the surgical buttress may be formed using techniques within the purview of those skilled in the art, such as casting, molding and the like.

Any of the porous layers of the surgical buttress may have openings or pores over at least a portion of a surface thereof. As described in more detail below, suitable materials for forming a porous layer include, but are not limited to fibrous structures (e.g., knitted structures, woven structures, non-woven structures, etc.) and/or foams (e.g., open or closed cell foams). In embodiments, the pores may be in sufficient number and size so as to interconnect across the entire thickness of the porous layer. Woven fabrics, knitted fabrics and open cell foam are illustrative examples of structures in which the pores can be in sufficient number and size so as to interconnect across the entire thickness of the porous layer. In embodiments, the pores may not interconnect across the entire thickness of the porous layer, but rather may be present at a portion thereof. Thus, in some embodiments, pores may be located on a portion of the porous layer, with other portions of the porous layer having a non-porous texture. Those skilled in the art reading the present disclosure will envision a variety of pore distribution patterns and configurations for the porous layer. Closed cell foam or fused non-woven materials are illustrative examples of structures in which the pores may not interconnect across the entire thickness of the porous layer.

Where a porous layer of the surgical buttress is fibrous, the fibers may be filaments or threads suitable for knitting or weaving or may be staple fibers, such as those frequently used for preparing non-woven materials. Suitable techniques for making fibrous structures are within the purview of those skilled in the art.

Where a porous layer of the surgical buttress is a foam, the porous layer may be formed using any method suitable to forming a foam or sponge including, but not limited to the lyophilization or freeze-drying of a composition. Suitable techniques for making foams are within the purview of those skilled in the art.

The origin and types of collagens that may be used to form the porous layer are the same as those indicated above for the non-porous layer. However, the oxidized or non-oxidized collagen may be lyophilized, freeze-dried, or emulsified in the presence of a volume of air to create a foam and then freeze-dried, to form a porous compress.

In embodiments, a porous layer of the surgical buttress may be made from denatured collagen or collagen which has at least partially lost its helical structure through heating or any other method. The term "denatured collagen" means collagen which has lost its helical structure. The collagen used for the porous layer as described herein may be native collagen or atellocollagen. The collagen may have been previously chemically modified by oxidation, methylation, succinylation, ethylation or any other known process.

The porous layer(s) may enhance the ability of the surgical buttress to absorb fluid, reduce bleeding, and seal the wound. Also, the porous layer(s) may allow for tissue ingrowth to fix the surgical buttress in place.

Figure 3A:
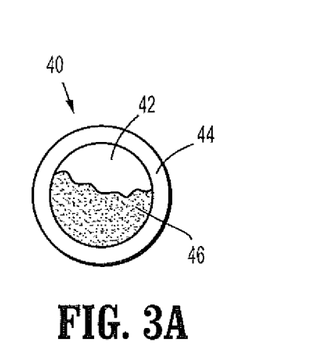
FIGS. 3A-3D schematically illustrate microbeads for use and incorporation in the surgical buttress of FIGS. 1 and 2, in accordance with embodiments of the present disclosure.
Figure 3B:
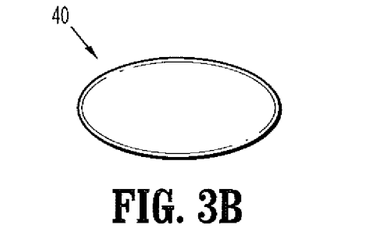
Figure 3C:
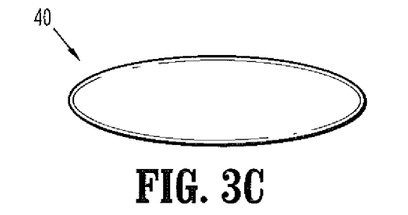
Figure 3D:
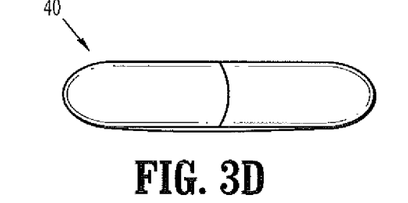

In accordance with the present disclosure, as seen in FIGS. 2-3D, microbeads 40 are incorporate into and/or onto at least a portion of surgical buttress 24 in a systematic or random distribution pattern. As illustrated in FIG. 3A, in an embodiment, each microbead 40 includes a casing 44 made from a polymeric material and which defines a core 42. It is contemplated that core 42 of microbeads 40 may contain a quantity of a hemostatic agent 46 therein. In embodiments, microbeads 40 are disposed on at least a portion of the inwardly facing or tissue facing surface 24b of surgical buttress 24 in order to ensure contact of the microbeads 40 with tissue. Examples of other suitable hemostatic agent filled materials include, for example, microspheres, liposomes, pellets, capsules, and the like.

The polymeric casing 44 may be formed from bioabsorbable materials, such as those described above. The bioabsorption profile, stress response profile, or degree of elasticity of the polymeric casing 44 may be controlled by polymer selection and casing construction. One of ordinary skill in the art will appreciate that the behavior of the polymer or copolymer forming the polymeric casing 44 depends on several factors, such as the chemical composition, the molecular weight of the polymer, and the degree of crystallinity. The degradation or bioabsorption kinetics and in vivo mechanical performance of the polymeric casing 44 may also be controlled by tailoring the size, wall thickness, surface topography, and diameter of the polymeric casing 44.

The microbeads 40 may be formed in a variety of sizes and shapes. In embodiments, microbeads 40 may be formed to have an overall diameter of between about 0.01 mm and about 3.0 mm, in embodiments, less than about 1.0 mm. In embodiments, microbeads 40 may be spherical, ellipsoid, elongated ellipsoid, and capsule shaped as illustrated in FIGS. 3A-3D, respectively. Thus, the composition of the polymeric casing 44 as well as the physical diameter, shape, and wall thickness of the polymeric casing 44 may be tailored to achieve the desired release profile of hemostatic agent 46 disposed therein.

As mentioned above, polymeric casing 44 of each microbead 40 is filled with hemostatic agent 46. In embodiments, the hemostatic agent 46 may be maintained in a fluid, hydrogel (in a flowable or non-state state), or solid (e.g., powder) state. Hemostatic agents include both natural and synthetic hemostats, and combinations thereof which may accelerate the process of blood clotting and provide a strong seal. Examples of natural hemostats include fibrin-based, thrombin-based, collagen-based, oxidized regenerated cellulose-based and gelatin-based natural hemostats, as well as aluminum alum (i.e., ammonium alum or aluminum ammonium sulfate). Hemostats herein also include astringents, e.g., aluminum sulfate, and coagulants.

Microbeads 40 may be incorporated into, or onto, a surface of the surgical buttress 24, or portion thereof, in a variety of ways. For example, the microbeads 40 may be applied via polymer coating, dry coating, freeze drying, blending, mixing, emulsifying, suspending, layering, partitioning, melt pressing, compressing, extruding, molding, impregnating, compounding, binding (e.g., ionic, covalent, or affinity binding), combinations thereof, and the like.

In embodiments, a coating may be applied utilizing any suitable coating method within the purview of those skilled in the art such as by spraying, dipping, vapor deposition, dusting, powder coating, rolling, brushing, immersion/wiping, melting, casting, electrostatic coating, electrospraying, ultrasonic spraying, combinations thereof, and the like.

In embodiments, the microbeads 40 may be freely admixed with the polymeric material forming the surgical buttress 24 or may be tethered to the surgical buttress 24 through any suitable chemical bonds. Admixed is understood to mean adding of the microbeads to the polymer for the surgical buttress and extruding the polymer and the microbeads together so that the microbeads are interspersed throughout the surgical buttress as the surgical buttress is manufactured. Tethered is understood to mean at least one of two things. First, tethered can mean that the surface of the microbeads can be treated so that the microbeads react favorably with the polymer for the surgical buttress to promote either adhesion or chemical reaction therebetween. Second, tethered can mean that an additive is added to the polymer of the surgical buttress that acts to grab (i.e., like a leash) the microbeads and keep the microbeads from being removed. In other embodiments, microbeads 40 may be embedded within the polymeric material forming the surgical buttress 24 and cured after embedding. In yet other embodiments, the microbeads 40 may be coated on a lyophilized foam.

In use, as illustrated in FIG. 4, the anvil jaw member 20 and the staple cartridge jaw member 22 including a staple cartridge 32, which has been loaded with a surgical buttress 24, are positioned on either side of the surgical site where adjacent layers of tissue "T" are to be fastened to one another. In accordance with the present disclosure, the construction of the microbeads 40 in surgical buttress 24 is such that microbeads 40 will resist rupturing until the surgical stapling apparatus 10 is fired and local force is applied to the microbeads 40. In embodiments, however, the microbeads 40 may be constructed to selectively rupture during insertion of the surgical stapling apparatus 10 through a trocar (not shown) during placement of the jaw assembly 16 at the surgical site and/or during grasping and manipulation of tissue "T" by a clinician.

As best shown in FIG. 5, staple cartridge 32 includes staples 50 positioned within individual staple pockets 52. Staples 50 are of a conventional type and include a backspan 54 having a pair of legs 56 and 58 extending from backspan 54. Legs 56 and 58 terminate in tissue penetrating tips 60 and 62, respectively. Pushers 64 are located within staple pockets 52 and are positioned between staples 50 and the path of a drive bar 66.

Surgical stapling apparatus 10 is initially actuated by movement of trigger 33 relative to handle 12 (FIG. 1) causing driver 36 to move in the direction of arrow "A" (FIG. 4), and against sloped edge 21 of anvil jaw member 20 thereby causing anvil jaw member 20 to be moved to the closed position relative to staple cartridge jaw member 22. As anvil jaw member 20 closes against staple cartridge jaw member 22, all or a portion of microbeads 40 rupture upon application of pressure thereto by the approximation of anvil jaw member 20 and staple cartridge jaw member 22. Accordingly, upon meeting a threshold pressure, microbeads 40 will rupture, break, split, fail, be crushed or otherwise open to release hemostatic agent 46. In embodiments, microbeads 40 may be mechanically similar such that the microbeads 40 have substantially the same rupture response. In other embodiments, a distribution of microbeads 40 having different mechanical characteristics (e.g., larger/smaller microbeads, thinner/thicker polymeric casings, etc.) may be incorporated into the surgical buttress 24 to provide a varied rupture response.

Figure 6:
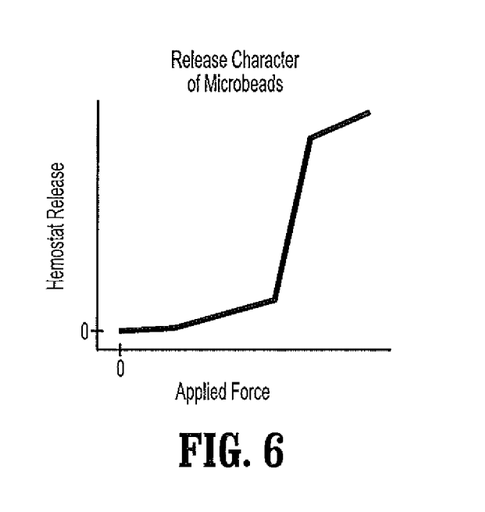
FIG. 6 illustrates a theoretical hemostatic agent release curve from a surgical buttress of the present disclosure during a stapling process.

As drive bar 66 advances distally within staple cartridge 32, drive bar 66 urges pushers 64 upwardly against backspan 54 of staples 50 driving legs 56 and 58 of staples 50 through surgical buttress 24, tissue "T", and towards staple forming pockets 68 in anvil jaw member 20. Tissue penetrating tips 60 and 62 of staple legs 56 and 58 are bent within staple forming pockets 68 in anvil jaw member 20 with backspan 54 securing surgical buttress 24 against tissue "T". When the pressure exerted between anvil jaw member 20 and staple cartridge jaw member 22 during the stapling procedure meets or exceeds the force or pressure required to rupture the microbeads 40, the microbeads 40 rupture to release the hemostatic agent 46 therefrom, directly at the staple line, as illustrated in the theoretical hemostatic agent release curve provided in FIG. 6.

In embodiments, the percentage of microbeads 40 that rupture during staple firing may be between about 10% to about 95%, in embodiments, from about 70% to about 90%. The polymeric casing 44 of the remaining intact microbeads 40 will degrade and/or dissolve with time and release hemostatic agent 46 without adverse side effect. Thus, in embodiments, the stapling process may provide an initial burst release of hemostatic agent by rupturing a portion of the microbeads during actuation of the surgical stapling apparatus, followed by a sustained release of hemostatic agent via the dissolution of the remaining intact microbeads.

In embodiments, one or more different microbeads may be incorporated into the surgical buttress. For example, the microbeads may contain the same hemostatic agent and polymeric casing, but differ in size and shape thereby affecting the compression force required to open/rupture the microbeads and thus, the release of the hemostatic agent therefrom. As such, relatively larger microbeads 40 may open/rupture prior to relatively smaller microbeads 40 as a result of the compressive forces acting thereon by the clamping/approximation of anvil jaw member 20 and staple cartridge jaw member 22. As another example, the microbeads may include different hemostatic agents and/or concentrations thereof.

In addition to polymer selection as described above, the rate of release of the hemostatic agent from the microbeads and/or surgical buttress may be controlled by other means within the purview of one skilled in the art. Some examples include, but are not limited to, the depth of the hemostatic agent from the surface of the surgical buttress or the thickness of the polymeric casing; the size of the hemostatic agent; the hydrophilicity or lipophilicity of the hemostatic agent; the pH and/or the ionization of the hemostatic agent/polymeric casing; and the strength of physical and physical-chemical interaction between the hemostatic agent/polymeric casing/surgical buttress. By properly controlling one or more of these factors, the rate of release and any lag time prior to release of a hemostatic agent from a buttress of the present disclosure may be controlled.

While not specifically shown, upon full actuation of surgical stapling apparatus 10, a knife blade associated with surgical stapling apparatus 10 and carried by driver 36 cuts tissue "T", as well as surgical buttress 24 between the rows of now formed staples 50. Upon movement of anvil jaw member 20 to the open position spaced apart from staple cartridge jaw member 22, surgical buttress 24 pulls away from anvil jaw member 20 and staple cartridge 32 of staple cartridge jaw member 22.

Figures 7A, 7B:
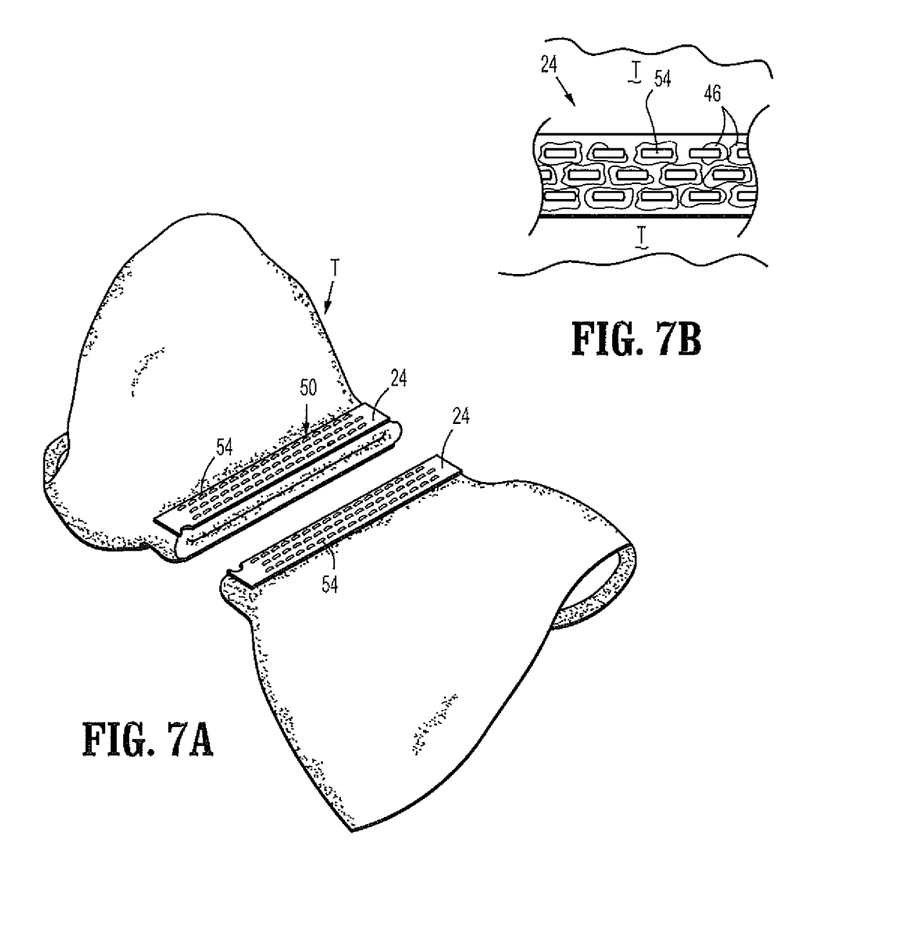
FIG. 7A is a perspective view of a stapled and divided tissue section.
FIG. 7B is an enlarged plan view of the stapled surgical buttress on a tissue section of FIG. 7A.

The resulting tissue "T", divided and stapled closed with staples 50, is best illustrated in FIG. 7A. Specifically, surgical buttress 24 is secured against tissue "T" by backspans 54 of staples 50. The bloom of released hemostatic agent 46 from the microbeads 40 after stapling is illustrated in FIG. 7B. Thus, surgical buttress 24 is stapled to tissue "T" thereby sealing and reinforcing the staple lines created by staples 50.

While compressive force is all that is required to break the microbeads 40, additional or alternative mechanisms may be employed, such as staple firing and puncturing of a surgical buttress or breaking individual enlarged microbeads with staples, examples of which are illustrated in FIGS. 8-11.

Figure 8:
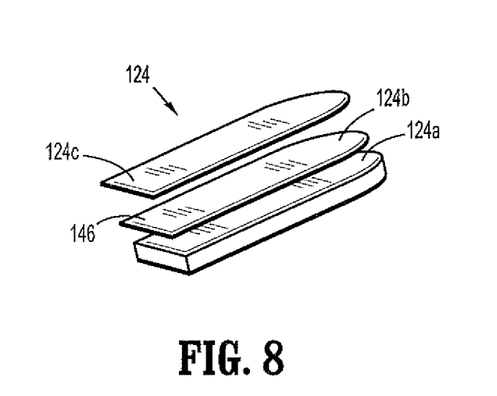
FIG. 8 is a schematic perspective view, with parts separated, of a multilayered surgical buttress in accordance with an embodiment of the present disclosure.

Turning now to FIG. 8, a multilayered surgical buttress 124 in accordance with an embodiment of the present disclosure is illustrated. Surgical buttress 124 includes a first layer 124a which may be porous or non-porous as described above, a second layer 124b including a hemostatic agent 146 covering first layer 124a, and a third layer 124c of inert, non-porous material covering second layer 124b.

In embodiments, the first layer 124a is an oxidized cellulose. Oxidized cellulose is capable of acting as a hemostatic agent and absorbing fluids, such as blood. The second layer 124b may be fabricated from polyethylene glycol and contain a hemostatic agent 146 therein and/or thereon. The hemostatic agent 146 may be contained within a microbead as described above, or may be freely admixed or tethered through chemical bonds with the polyethylene glycol forming the second layer 124b. As the hemostatic agent 146 is disposed within or on the second layer 124b, the hemostatic agent 146 will activate by the application of fluid thereto as polyethylene glycol is capable of absorbing fluids. The third layer 124c may this be provided as a barrier protecting the second layer 124b against exposure to or contact with moisture.

The multilayer surgical buttress 124 described herein may be prepared by attaching the individual layers 124a, 124b, and 124c together to form a multiple layer surgical buttress. The multilayer surgical buttress 124 may be formed or assembled using any method known to those skilled in the art. It is envisioned that the layers of the surgical buttress may be adhered to one another using chemical bonding, surgical adhesives, surgical sealants, and surgical glues. In addition, the layers may be bound together using mechanical means such as stitchings, pins, rods, screws, clips, etc. Still further, the layers may naturally, or through chemical or photoinitiation, interact and crosslink or provide covalent bonding therebetween.

Figure 9:
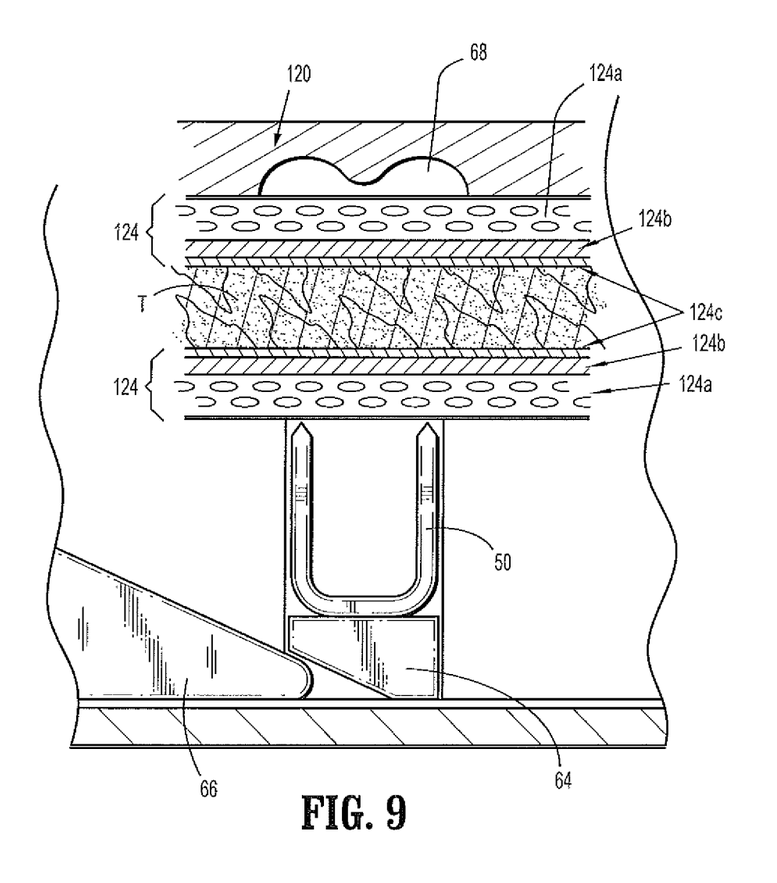
FIG. 9 is a cross-sectional view of the multilayered surgical buttress of FIG. 8 loaded into a surgical stapling apparatus.

As seen in FIG. 9, surgical buttress 124 of FIG. 8 is shown disposed on both the anvil jaw member 20 and the staple cartridge 32 of staple cartridge jaw member 22 of surgical stapling apparatus 10. As illustrated, the surgical buttress 124 is disposed on anvil jaw member 20 and/or staple cartridge 34 of surgical cartridge jaw member 22 such that the third layer 124c of inert material contacts tissue "T" during actuation of surgical stapling apparatus 10. The third layer 124c thus prevents the release or activation of the hemostatic agent 146 from the second layer 124b during introduction and manipulation of the surgical stapling apparatus within the surgical site. Once penetrated by staples 50, physiological fluids from tissue "T" will be driven into the second layer 124b by the high clamping pressure between the anvil jaw member 20 and staple cartridge jaw member 22, as well as by the perforations created by staples 50. The physiological fluid will be absorbed by and pass through the polyethylene glycol within second layer 124b, thereby allowing for the migration of the hemostatic agent 146 into tissue "T".

Figure 10:
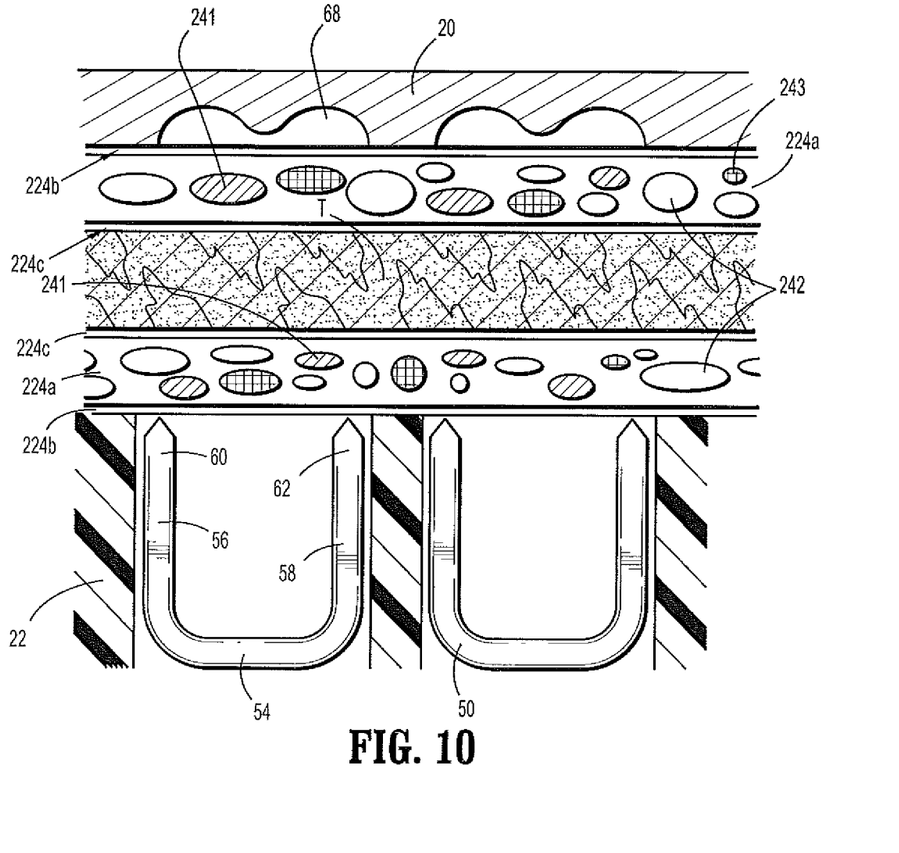
FIG. 10 is a cross-sectional view of a multilayered surgical buttress in accordance with another embodiment of the present disclosure loaded into a surgical stapling apparatus.

Turning now to FIG. 10, another embodiment of a surgical buttress 224 is illustrated positioned on both the anvil jaw member 20 and the staple cartridge 34 of staple cartridge jaw member 22 of surgical stapling apparatus 10. Surgical buttress 224 includes reservoirs of tissue sealants 241, hemostats 242, and/or other bioactive agents 243 disposed within a first layer 224a of non-porous or porous material. In embodiments, the sealant 241, hemostat 242, and other bioactive agent 243 may be encapsulated by a polymeric casing to form a microbead. In other embodiments, the sealant 241, hemostat 242, and other bioactive agent 243 may be freely disposed within pockets formed within the polymer of first layer 224a. In yet other embodiments, combinations of encapsulated and free sealant, hemostats, and bioactive agents may be uniformly or randomly distributed through first layer 224a.

As illustrated in the present embodiment, a first layer 224a is protected by second and third non-porous layers 224b and 224c. It is envisioned that first layer 224a may include a non-porous third layer 224c on just a tissue facing surface of the surgical buttress 224 as described above. Alternatively, in embodiments in which first layer 224a is non-porous, surgical buttress 224 may not contain a separate non-porous layer.

Figure 11:
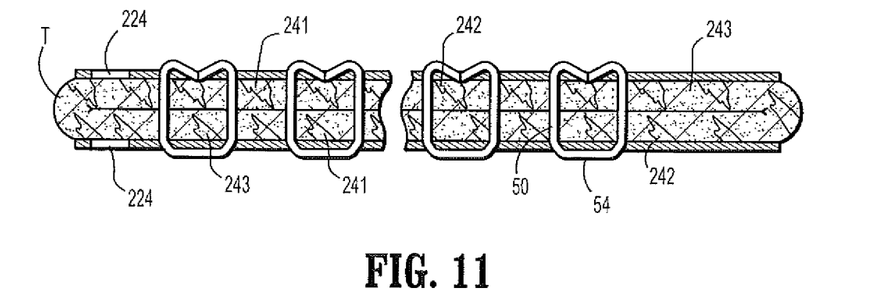
FIG. 11 is a cross-sectional view of the stapled tissue of FIG. 10.

In use, upon actuation of surgical stapling apparatus 10, the legs 56 and 58 of staples 50 will pierce first layer 224a of surgical buttress 224 thereby releasing the sealant 241, hemostat 242, and/or other bioactive agents 243 around the perforations created by the penetrating tips 60 and 62 of staples 50 and through first layer 224a thereby providing contact with the tissue "T".

In embodiments, at least one bioactive agent may be combined with the surgical buttress and/or any of the individual components (a porous layer, a non-porous layer, a hemostatic agent, polymeric casing of a microbead, etc.) used to construct the surgical buttress. In these embodiments, the surgical buttress can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the surgical buttress in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Other bioactive agents which may be included as a bioactive agent in the surgical buttress of the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

In embodiments, a reinforcement member may be positioned within or over the surgical buttress. In embodiments utilizing a multilayered surgical buttress, one or more reinforcement members may be positioned between, within, or at an external surface of a layer of the surgical buttress as are disclosed, for example, in U.S. Patent Application Publication No. 2009/0001122 filed Jun. 27, 2007, entitled "Buttress and Surgical Stapling Apparatus," the entire disclosure of which is incorporated by reference above.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A surgical stapling apparatus, comprising:
    a jaw assembly including a pair of jaw members; and
    a surgical buttress positioned adjacent a tissue contacting surface of at least one of the pair of jaw members, the surgical buttress comprising a plurality of microbeads each having a polymeric casing defining a core containing a hemostatic agent therewithin, at least a portion of the plurality of microbeads being configured to rupture and release the hemostatic agent therefrom upon actuation of the surgical stapling apparatus to approximate the pair of jaw members and exert a pressure on the surgical buttress, the microbeads having a predetermined rupturing force.

2. The surgical stapling apparatus of claim 1, wherein the polymeric casing is fabricated from a bioabsorbable material.

3. The surgical stapling apparatus of claim 2, wherein the polymeric casing of a remaining portion of the plurality of microbeads are configured to degrade and release the hemostatic agent over time.

4. The surgical stapling apparatus of claim 1, wherein the microbeads are about 0.01 mm to about 3.0 mm in diameter.

5. The surgical stapling apparatus of claim 1, wherein the microbeads are less than about 1.0 mm in diameter.

6. The surgical stapling apparatus of claim 1, wherein the microbeads are configured in a shape selected from the group consisting of spherical, ellipsoid, elongated ellipsoid, capsule, and combinations thereof.

7. The surgical stapling apparatus of claim 1, wherein the hemostatic agent is disposed within the plurality of microbeads of the surgical buttress in a non-solid state.

8. The surgical stapling apparatus of claim 1, wherein the microbeads containing the hemostatic agent is freely admixed with a polymer forming the surgical buttress.

9. The surgical stapling apparatus of claim 1, wherein the surgical buttress further comprises a sealant, the surgical buttress being configured to release the sealant therefrom upon actuation of the surgical stapling apparatus to approximate the pair of jaw members and exert a pressure on the surgical buttress.

10. The surgical stapling apparatus of claim 1, wherein the surgical buttress further comprises a bioactive agent, the surgical buttress being configured to release the bioactive agent upon actuation of the surgical stapling apparatus to approximate the pair of jaw members and exert a pressure on the surgical buttress.

11. The surgical stapling apparatus of claim 1, wherein the surgical buttress includes a first layer containing the plurality of microbeads containing the hemostatic agent and a second layer of non-porous material positioned adjacent to the first layer.

12. The surgical stapling apparatus of claim 11, wherein the surgical buttress further comprises a third layer of porous or non-porous material positioned adjacent to the first layer.

13. A surgical stapling apparatus, comprising:
    a jaw assembly including a staple forming anvil jaw member and a staple cartridge jaw member;
    a trigger for actuating the jaw assembly between an open position where the anvil jaw member and the staple cartridge jaw member are spaced apart from one another and a closed position where the anvil jaw member and the staple cartridge jaw member are substantially adjacent to one another and for applying at least one row of staples to tissue when the jaw assembly is in the closed position; and
    a surgical buttress positioned adjacent a tissue contacting surface of at least one of the anvil jaw assembly or the staple cartridge jaw assembly, the surgical buttress containing a plurality of microbeads each having a bioabsorbable polymeric casing defining a core containing a hemostatic agent therewithin, at least a portion of the plurality of microbeads being configured to rupture and release the hemostatic agent subsequent to actuation of the trigger and approximation of the jaw assembly to the closed position, and the polymeric casing of a remaining portion of the microbeads being configured to degrade and release the hemostatic agent over time, the polymeric casing having a predetermined rupturing force.

14. The surgical stapling apparatus of claim 13, wherein when the jaw assembly is disposed in the closed position about 10% to about 95% of the hemostatic agent is released.

15. The surgical stapling apparatus of claim 13, wherein when the jaw assembly is disposed in the closed position about 70% to about 90% of the hemostatic agent is released.

16. The surgical stapling apparatus of claim 13, wherein the hemostatic agent is released in response to a compressive force of the jaw assembly against tissue positioned between the anvil jaw member and the staple cartridge jaw member.

17. The surgical stapling apparatus of claim 13, wherein the hemostatic agent is released upon passage of a staple from a staple cartridge loaded in the staple cartridge jaw member through the surgical buttress.

18. A staple cartridge, comprising:
    a staple cartridge containing a plurality of staples for use in a surgical stapling apparatus; and
    a surgical buttress disposed on a tissue contacting surface of the staple cartridge and being releasably affixed to the staple cartridge, the surgical buttress comprising a layer of polymeric material including a plurality of microbeads each having a polymeric casing defining a core containing a hemostatic agent therewithin, at least a portion of the plurality of beads being configured to rupture and release the hemostatic agent therefrom upon application of pressure thereto, the microbeads having a predetermined rupturing force.

19. The staple cartridge of claim 18, wherein the microbeads are disposed within the layer of polymeric material.

20. The staple cartridge of claim 18, wherein the microbeads are disposed on a surface of the layer of polymeric material.

21. The staple cartridge of claim 18, wherein the surgical buttress further comprises a second layer of polymeric material adjacent the layer of polymeric material including the hemostatic agent.

\* \* \* \* \*